United States Patent [19]
Kaneko

[11] Patent Number: 5,397,535
[45] Date of Patent: Mar. 14, 1995

[54] AGGREGATE FOR CONSTRUCTION MATERIAL FROM INFECTIOUS MEDICAL WASTE ARTICLES

[76] Inventor: Tadashi Kaneko, 3906-20, Akuwamachi, Seya-ku, Yokohama, Kanagawa 246, Japan

[21] Appl. No.: 968,864

[22] Filed: Oct. 30, 1992

Related U.S. Application Data

[63] Continuation-in-part of Ser. No. 793,429, Dec. 17, 1991, abandoned.

[51] Int. Cl.⁶ .................. A61L 2/04; B01J 2/10
[52] U.S. Cl. .................. 422/22; 422/32; 422/309; 422/900; 241/23; 241/606
[58] Field of Search ........... 422/3, 22, 32, 38, 287, 422/292, 307, 309, 900, 286, 184; 241/23, 98, DIG. 38, 606; 588/257, 901

[56] References Cited

U.S. PATENT DOCUMENTS

| | | | |
|---|---|---|---|
| 4,706,893 | 11/1987 | Brock | 241/23 |
| 4,860,958 | 8/1989 | Yerman | 241/23 |
| 4,919,722 | 4/1990 | Trivino Vazquez et al. | 241/DIG. 38 X |
| 5,035,367 | 7/1991 | Nojima | 241/DIG. 38 X |
| 5,048,766 | 9/1991 | Gaylor et al. | 241/606 X |

FOREIGN PATENT DOCUMENTS 9012251 10/1990 WIPO ................ 422/184

Primary Examiner—Robert J. Warden
Assistant Examiner—E. Leigh Dawson
Attorney, Agent, or Firm—Lorusso & Loud

[57] ABSTRACT

Various kinds of used and potentially infectious medical articles such as injection needles are first crushed into pieces to such an extent that the shape of the articles can not be visually identified. Subsequently, the crushed medical articles and particulate absorbent are introduced into a mixer and mixed and heated therein to a temperature above 180° C. by use of a heater in combination with frictional heat generated as the mixer blade is rotated, whereby the crushed infectious medical waste articles are completely sterilized. The particulate absorbent serves to absorb any unpleasant odor or toxic gas which is generated from the crushed infectious medical articles during heating. In such manner, sterilization of the crushed infectious medical appliances and absorption of the toxic gas can simultaneously be achieved, and moreover, the resultant sterile admixture can be used as an aggregate for construction material such as concrete.

8 Claims, 3 Drawing Sheets

AGGREGATE FOR CONSTRUCTION MATERIAL FROM INFECTIOUS MEDICAL WASTE ARTICLES

CROSS-REFERENCE TO RELATED APPLICATION

This is a continuation-in-part of U.S. application Ser. No. 07/793,429, filed Dec. 17, 1991, now abandoned and entitled "Apparatus for Producing Aggregate for Construction Works from Infectious Medical Waste Articles".

BACKGROUND OF THE INVENTION

Field of the Invention

The present invention relates to a method and apparatus for producing a novel aggregate employable for construction work from infectious medical waste articles, derived from hospitals and other sources, by sterilizing, without necessity for burning, and to the novel aggregate so produced.

Background

As is well known, various kinds of so-called infectious medical waste articles such as syringes, injection needles and the like are discarded by hospitals as waste. Since there is a danger that infectious bacilli adhere to such infectious medical waste articles, disposal of the infectious medical waste articles in the same manner as ordinary waste is strictly prohibited. For this reason, personnel in hospitals collect infectious medical waste articles in a special container exclusively employed for that purpose and then transport the container to a disposal installation located outside of the hospital where the waste is burned and thereby sterilized. However, since injection needles and the like retain their shape even after completion of the burning, they can be visually identified. Infectious medical waste articles should be transported to a controlled disposal installation for the purpose of thermal disposal and the cost of such disposal is higher than that for ordinary waste disposal in an ordinary disposing installation.

Since infectious bacilli can be killed at any temperature higher than 180° C., it suffices to heat infectious medical waste articles up to a temperature higher than 180° C. for sterilization without necessity for burning. However, due to the fact that various kinds of foreign materials, e.g., synthetic resins such as polyvinyl chloride resin, polypropylene resin, acrylonitrile-butadiene-styrene copolymer resin and the like, and rubber and metallic materials are contained in the infectious medical waste articles, an unpleasant odor is generated as they are heated at a temperature higher than 160° C. In addition, a toxic gas such as chlorine gas or the like is generated as they are incinerated. As far as a conventional method of sterilizing infectious medical waste articles merely by heating is concerned, the resulting unpleasant odor and toxic gas cannot be eliminated at an acceptable cost. For this reason, it is unavoidable that such hospital waste materials be disposed in the manner mentioned above, i.e. by incineration in a combustion type installation.

It should be added that disposal of infectious medical waste articles by an unauthorized operator is strictly prohibited, and moreover, combustion cost and transportation cost are higher than required for disposing of ordinary waste, resulting in an economical burden to be borne by a hospital or like facility.

Since no use for waste infectious medical articles has hitherto been proposed, governmental organizations are required to yearly increase the number of controlled disposal installations for special waste articles. However, in practice, it is difficult to increase the number of disposal installations of the foregoing type and to acquire land for building additional disposal installations.

The present invention has been made in consideration of the foregoing background and has as its object to provide an apparatus and method for producing a useful sterilized product, employable as an aggregate for construction work, from waste infectious medical articles by heating without generation of an unpleasant odor or toxic gas.

SUMMARY OF THE INVENTION

The apparatus of the present invention, for producing an aggregate employable for construction work from infectious medical waste articles, includes a crusher for crushing the infectious medical waste articles, a mixer for mixing the crushed infectious medical waste articles with a particulate catalyzer (absorbent) effective for absorbing gas generated from the waste articles at elevated temperature, and heating means for heating the mixer.

The process of the present invention involves crushing the used medical articles to an extent that the medical articles can no longer be visually identified, admixing the crushed medical articles with a particulate absorbent for noxious gases and heating the admixture at a temperature above 180° C. to sterilize the crushed medical articles, while noxious gases evolve from the medical articles are absorbed by the particulate absorbent. Preferably, the heating and mixing steps are simultaneously conducted. An important advantage of this process is that it allows for sterilization within a 10 minute period. Sterilization can be suitably effected with simultaneous heating and mixing within a period of 5-10 minutes.

The amount of the particulate absorbent is preferably 20-70 wt. % of the admixture. The preferred absorbent is calcium carbonate or limestone.

The present invention also relates to a novel aggregate comprising sterile, crushed medical articles and a particulate inorganic compound capable of absorbing acidic gases. The particulate inorganic compound preferably constitutes 20-70% by weight of the aggregate material and is preferably calcium carbonate or limestone.

The terminology "infectious medical waste article" as used herein, is intended to have reference to used appliances and bandages which have come into contact with human blood and/or other human body fluids and are thereby potentially contaminated with infectious microorganisms and/or viruses. Such articles may include, for example, used syringes (plastic and/or glass) and injection needles.

DESCRIPTION OF THE PREFERRED EMBODIMENTS

The present invention will now be explained with reference to the accompanying drawings which illustrate a preferred embodiment of the present invention.

Figure 1:
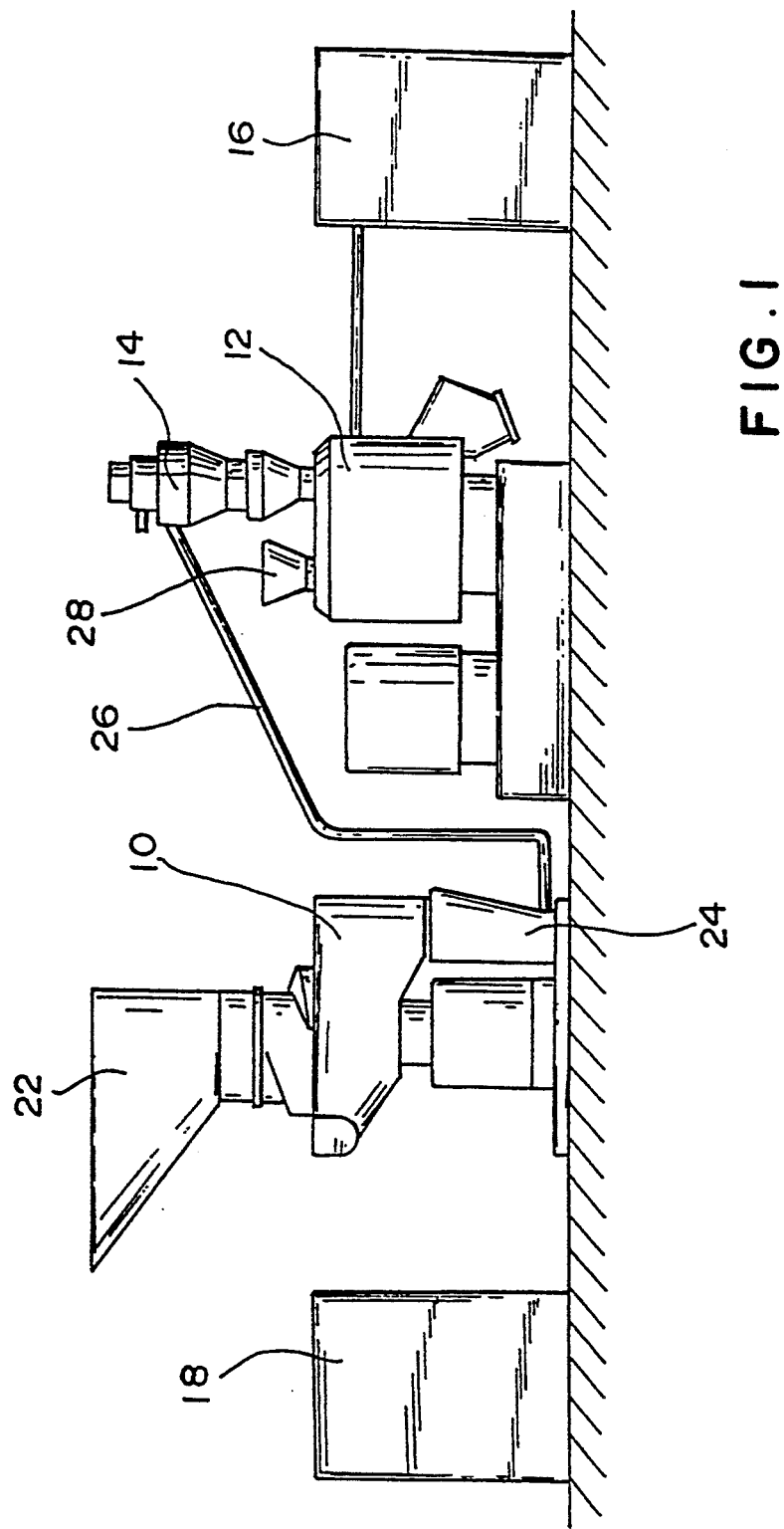
FIG. 1 is a side view which schematically illustrates in a disassembled state the structure of an apparatus for sterilizing infectious medical waste articles, without burning, in accordance with an embodiment of the present invention.
Figure 2:
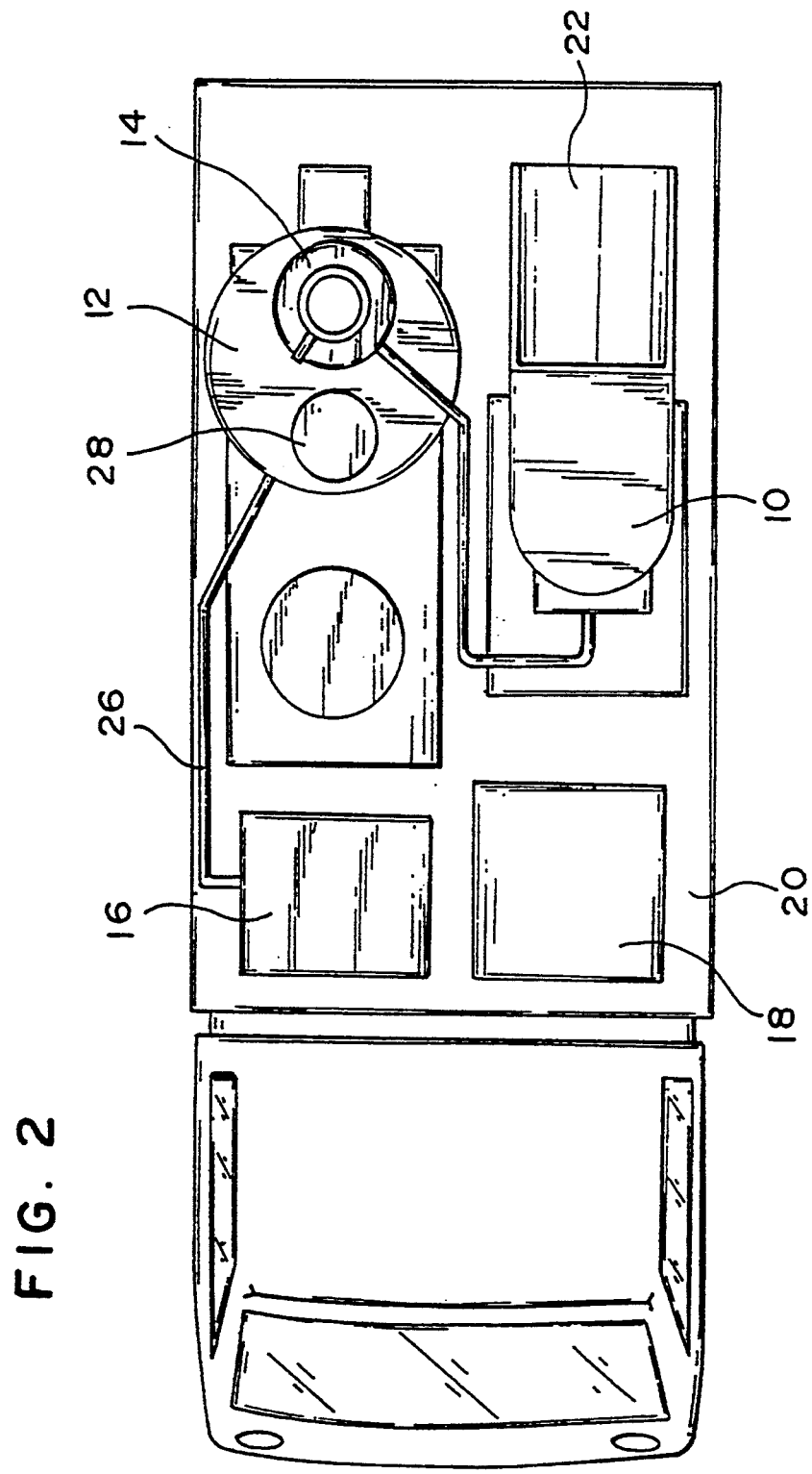
FIG. 2 is a plan view of the apparatus in FIG. 1, mounted on a vehicle.

As shown in FIGS. 1 and 2, the apparatus is essentially composed of a crusher 10 for crushing infectious medical waste articles into pieces, a mixer 12, a suction unit 14 for introducing the crushed waste articles into the mixer 12, an oil recirculation type heating unit 16 for heating the mixer 12, and a generator 18 serving as a power supply source for all the above-mentioned components. These components are mounted on an automotive vehicle 20 such as a truck or the like as shown in FIG. 2.

As various kinds of infectious medical waste articles are supplied into the crusher 10 from a hopper 22 arranged above the crusher 10, they are crushed into pieces in the crusher 10 and the crushed pieces are stored in a storage chamber 24 located below the crusher 10. Infectious medical waste articles are crushed into pieces in the crusher 10 so that injection needles and the like are converted into a safe form and into a shape which cannot be visually identified. For this reason, the resultant product obtained by way of the foregoing steps can be utilized as an aggregate for a construction material. The suction unit 14 mounted on the mixer 12 communicates with the storage chamber 24 of the crusher 10 via a duct 26. As the suction unit 14 is activated, the infectious medical waste articles which have been crushed in the crusher 10 are pneumatically conveyed from the chamber 24 into the mixer 12.

Figure 3:
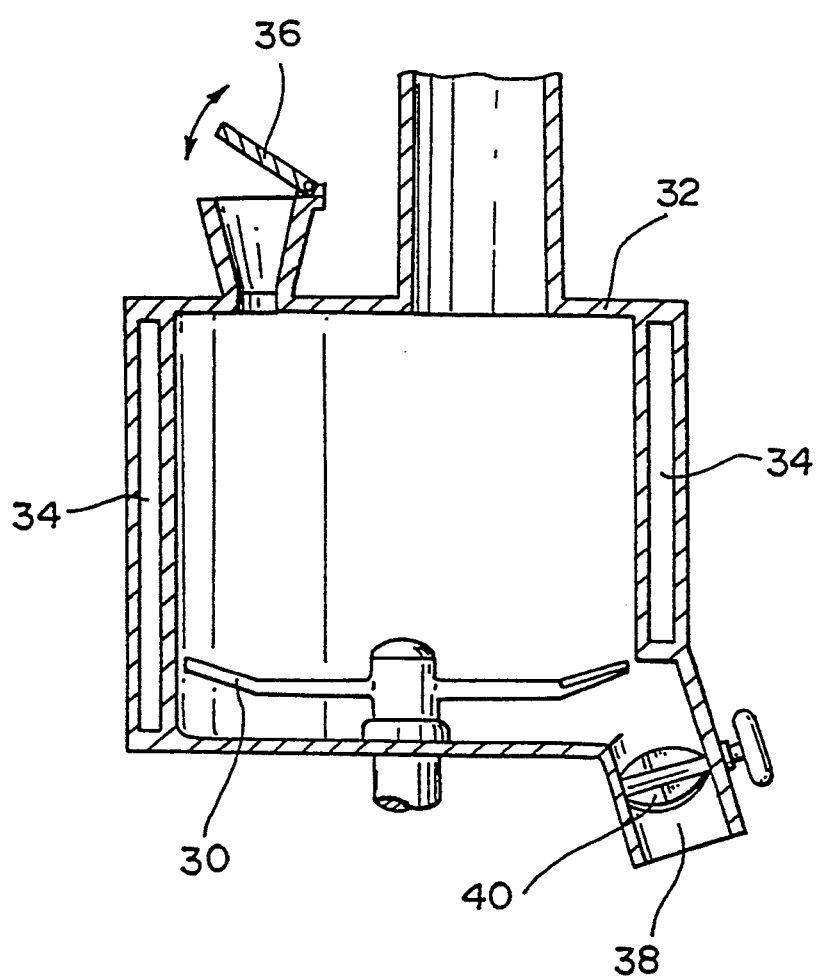
FIG. 3 is a sectional side view of the mixer of the apparatus of FIG. 1.

As shown in FIG. 1, a hopper 28 is mounted on the upper surface of the mixer 12 so that the particulate absorbent can be introduced into the mixer 12. Referring to FIG. 3, the mixer 12 is equipped with a rotary blade 30 so that the crushed infectious medical waste articles and the particulate absorbent are vigorously stirred in the mixer 12 as the blade 30 is rotated. An oil recirculating passage 34 is formed around the side wall of a housing 32 of the mixer 12 so as to allow oil to flow through the recirculating passage 34. As the oil heated in the heater 16 is recirculated through the recirculating passage 34, the interior of the mixer 12 is heated by the hot oil. At this time, the hopper 28 is covered with a lid 36. A valve 40 is provided in an outlet port 38 off the bottom of the mixer 12. While the blade 30 is rotated and the hot oil is recirculated through the recirculating passage 34, the lid 36 and the valve 40 should be kept closed.

Next, operation of the above-described apparatus will be explained.

First, infectious medical waste articles such as bloody injectors, injection needles or the like are introduced into the crusher 10 so that they are crushed into pieces in the crusher 10 and thereby converted into a safe material of a shape which cannot be visually identified. This is to enable the crushed infectious medical articles to be utilized as an aggregate for a construction material after sterilization.

Before the crushed infectious medical waste articles are introduced into the mixer 12, particulate absorbent is supplied into the mixer 12 from the hopper 28, and thereafter, the hopper 28 is air-tightly closed with the lid 36. It should be noted that the absorbent is selected to provide material having two functions, i.e. (1) to assure that particles derived from the crushed infectious medical waste articles do not adhere as deposits on the inner wall of the mixer 12 and (2) to assure that an unpleasant odor generated from rubber based infectious medical waste articles at a temperature higher than 160° C. and toxic gas, such as chlorine gas or the like generated when a polyvinyl chloride or similar resin is burned, are completely absorbed in the particulate absorbent. Preferably, the absorbent is an inorganic compound capable of absorbing acidic gases. It has been found that calcium carbonate is most preferably employed as the particulate absorbent. In addition to the aforementioned advantages, the calcium carbonate is available at an inexpensive cost, e.g. as limestone, and moreover, can be used as an aggregate for increasing the strength of a concrete.

As a hot oil heated in the heater 16 is introduced into the recirculating passage 34 arranged around the housing 32 of the mixer 12, the hot oil heats the mixer 12 to a temperature of about 150° C. so as not to allow an unpleasant odor or a toxic gas to be generated from the crushed infectious medical waste articles. After completion of the heating operation, the infectious medical waste articles crushed in the crusher 10 are conveyed to the mixer 12 via the duct 26 with the aid of the suction unit 14. When a predetermined quantity of crushed infectious medical waste articles has been introduced into the mixer 12, a communication port between the mixer 12 and the supply unit 14 is first closed. Subsequently, the blade 30 is rotated in the mixer 12 so that the crushed infectious medical waste articles and the particulate absorbent ("catalyzer") are mixed.

As the heated oil is recirculated through the recirculating passage 34, a mixture of the crushed infectious medical waste articles and the particulate absorbent is heated in the mixer 12 up to a temperature of about 150° C. Additionally, frictional heat is generated as the blade 30 is rotated in the mixer 12, whereby the mixture of the crushed infectious medical waste articles and the particulate absorbent is heated up to a temperature higher than 180° C. within a period of few minutes under the influence of the frictional heat. Once the crushed infectious medical waste articles have been heated up to a temperature higher than 180° C., infectious bacilli contained in the crushed infectious medical waste articles are completely killed. Although the mixture can be raised above 180° C. by use of the heater 16, the temperature to be reached by the heater 16 is set to about 150° C., since the temperature is elevated further by 30° C. or more merely by the frictional heat. When the temperature exceeds 160° C., an unpleasant odor and a toxic gas are generated from the crushed infectious medical waste articles but they are absorbed by the particulate catalyzer (absorbent). After the crushed infectious medical waste materials have been completely sterilized, the valve 40 is opened so that a mixture of the sterilized infectious medical waste articles and the particulate absorbent is discharged from the mixer 12 via the opening 38. The resultant product containing the sterilized infectious medical waste articles and the particulate absorbent discharged via the opening 38 is in the form of ball-shaped masses having a diameter of 5 mm to 2 cm. It has been confirmed that the ball-shaped agglomerates can safely be used as aggregate for concrete or similar construction material as is, since the infectious medical waste articles have been crushed and completely sterilized.

According to the present invention, when the apparatus is brought into a hospital, with the crusher 10, the mixer 12, the suction supply unit 14 and the oil recirculation type heater 16 mounted on an automotive vehicle 20 as shown in FIG. 3, various kinds of infectious medical waste articles can be processed by an unskilled operator. It should of course be understood that the present invention should not be limited to only the case where the crusher 10, the mixer 12, the supply unit 14 and the heater 16 are portably mounted on the automotive vehicle 20 but these components constituting the apparatus of the present invention may also be a stationary installation for practical use. As described above, with the apparatus and method of the present invention, various kinds of crushed infectious medical waste articles are mixed with particulate absorbent in the mixer and the resultant mixture is then thermally sterilized by heating it to a temperature of at least 180° C., with the aid of frictional heat generated during mixing as well as the heater. Unpleasant odors and toxic gas generated from the crushed infectious medical waste articles during the heating at an elevated temperature are effectively absorbed by the particulate absorbent. In contrast to the conventional processing method as described above, there is no need to incinerate infectious medical waste articles for the purpose of sterilization. Thus, the present invention provides a very economical system for use by hospitals, each of which has the task of disposing of their own infectious medical waste articles.

In addition, large expenditures have hitherto been required for conveying infectious medical waste articles to a combustion installation or a controlled dumping location. In contrast, with the present invention, infectious medical waste materials can be economically used as an aggregate for construction materials, e.g. concrete aggregate. Further, according to the present invention, however, each hospital can itself dispose of such articles, and moreover, any concern can perform the disposal operation on a the commercial basis to produce an aggregate employable for construction material from infectious medical waste articles, without the necessity of employing persons especially skilled in the handling of infectious materials.

The present invention also offers the hope that government organizations will not be required to increase the number of controlled dumping sites specially designated for the disposal of contaminated medical appliances.

Since calcium carbonate, if used as the particulate absorbent, is inexpensive and is widely available in the form of limestone, the resultant product which has been subjected to sterilizing and deodorizing offers a low cost and highly valuable aggregate for concrete.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A process for converting used medical articles into an aggregate for construction materials, said process comprising:
   providing used medical articles containing plastic components;
   crushing the used medical articles to the extent that the medical articles can no longer be visually identified;
   admixing the crushed medical articles with a particulate absorbent for gases to produce an admixture containing 20-70 wt. % of said particulate adsorbent; and
   heating the admixture at a temperature in excess of 180° C. to generate a toxic gas by burning said plastic components and to sterilize said admixture;
   aborbing the generated toxic gas with said particulate absorbent; and
   recovering the admixture after heating for use as a construction material.

2. The process of claim 1 wherein said admixing and said heating are conducted simultaneously for a period of 5-10 minutes.

3. The process of claim 1 wherein said particulate absorbent is a particulate calcium carbonate.

4. The process of claim 1 wherein said used medical articles comprise injection needles and syringes.

5. The process of claim 1 wherein the used medical articles include injection needles.

6. An aggregate for use in concrete comprising crushed and sterilized medical articles in admixture with an inorganic compound capable of absorbing acidic gases.

7. The aggregate of claim 6 wherein said inorganic compound is calcium carbonate or limestone.

8. A sterile aggregate suitable for use as a construction material produced by a process comprising:
   providing used medical articles containing plastic components;
   crushing the used medical articles to the extent that the medical articles can no longer be visually identified;
   admixing the crushed medical articles with a particulate absorbent for gases to produce an admixture containing 20-70 wt. % of said particulate adsorbent; and
   heating the admixture at a temperature in excess of 180° C. to generate a toxic gas by burning said plastic components and to sterilize said admixture;
   absorbing the generated toxic gas with said particulate absorbent; and
   recovering the admixture after heating for use as a construction material.

* * * * *

UNITED STATES PATENT AND TRADEMARK OFFICE
CERTIFICATE OF CORRECTION

PATENT NO. : 5,397,535
DATED : March 14, 1995
INVENTOR(S) : Kaneko et al.

It is certified that error appears in the above-indentified patent and that said Letters Patent is hereby corrected as shown below:

On title page, Item [30] Foreign Application Priority Data

June 18, 1990 ................ 2-157636--.

Signed and Sealed this

Thirty-first Day of October 1995

Attest:

BRUCE LEHMAN

Attesting Officer    Commissioner of Patents and Trademarks